(12) United States Patent
Jennings-Spring (10) Patent No.: US 6,580,011 B1
(45) Date of Patent: Jun. 17, 2003

(54) CIRCUMCISION/PENILE DRESSING (76) Inventor: Barbara Jennings-Spring, 10844 N. Dogwood Trail, Jupiter, FL (US) 33478

( * ) Notice: Subject to any disclaimer, the term of this patent is extended or adjusted under 35 U.S.C. 154(b) by 26 days.

(21) Appl. No.: 09/624,535

(22) Filed: Jul. 24, 2000

Related U.S. Application Data (60) Provisional application No. 60/146,392, filed on Jul. 29, 1999.

(51) Int. Cl.[7] ................................. A61F 13/00
(52) U.S. Cl. .......................... 602/41; 602/48
(58) Field of Search .................. 602/41, 900, 51, 602/48, 61–62, 67, 79; 128/885, DIG. 25; 2/21, 163; 604/358, 346–349

(56) References Cited

U.S. PATENT DOCUMENTS

| | | | |
|---|---|---|---|
| 2,646,796 A | | 7/1953 | Scholl |
| 4,176,664 A | * | 12/1979 | Kalish .................. 604/307 |
| 4,576,599 A | * | 3/1986 | Lipner .................. 604/390 |
| 4,983,163 A | * | 1/1991 | Winans .................. 604/49 |
| 5,085,210 A | | 2/1992 | Smith, III |
| 5,183,460 A | | 2/1993 | Scherz |
| 5,275,592 A | * | 1/1994 | Grizzaffi ............... 602/72 |
| 5,592,953 A | | 1/1997 | Delao |
| 5,797,401 A | | 8/1998 | Knight |
| 5,807,299 A | * | 9/1998 | McRoberts et al. ........... 602/67 |
| 5,817,038 A | * | 10/1998 | Orange et al. ............... 602/3 |
| 5,935,091 A | * | 8/1999 | Friedman .................. 602/79 |
| 5,947,998 A | * | 9/1999 | Cartmell et al. ........... 606/213 |
| 5,989,567 A | * | 11/1999 | Dolisi ..................... 424/400 |
| 6,068,607 A | * | 5/2000 | Palmer et al. ............. 602/67 |
| 6,307,118 B1 | * | 10/2001 | Reich ..................... 602/42 |

* cited by examiner

Primary Examiner—Nicholas D. Lucchesi
Assistant Examiner—Quang D Thanh
(74) Attorney, Agent, or Firm—Akerman Senterfitt (57) ABSTRACT

A dressing for a penis includes a sleeve bandage portion with outwardly extending securement straps. Fastening material can be affixed to the distal ends of the securement straps. The sleeve bandage portion can be configured to be placed on the circumcised penis so as to sheath the penis. After the sleeve bandage is placed on the penis, the dressing can be secured in place by diametrically wrapping the securement straps around the sleeve bandage by engaging the fastening material on the securement straps to the surface of the sleeve bandage. The bandage can be packaged in a hygienically sealed foil package openable at a top edge which allows the bandage to be removed with a minimal amount of handling. Topical antibiotics and anesthetics, as well as petroleum jelly, can be incorporated into the sleeve bandage.

22 Claims, 6 Drawing Sheets

CIRCUMCISION/PENILE DRESSING

CROSS REFERENCE TO RELATED APPLICATIONS

The present application claims the benefit of U.S. Provisional Application Serial No. 60/146,392 filed Jul. 29, 1999, which is incorporated herein by reference.

BACKGROUND OF THE INVENTION

1. Field of the Invention

This invention relates to post-operative wound dressings, and in particular to wound dressings to be applied to a penis.

2. Description of the Prior Art

Circumcision is one of the oldest of all surgical procedures, and is the operation most frequently performed on males in the United States. While circumcision is sometimes performed on adults and young children, the operation is most commonly performed on newborn infants.

As in any surgical procedure, there is a risk of infection associated with circumcision. Cleanliness and proper dressing of the wound site is of utmost importance. Bandages applied to the penile area are difficult to maintain, and the application of post-surgical dressings to infants presents particular problems. Ordinary strip gauze material and 4"×4" gauze is frequently used to bandage the newly circumcised penis of an infant. The necessity of simultaneously diapering the infant tends to interfere with the placement of the bandage, as the removal of the diaper may rip away the bandage. The delicacy of the operated area, as well as the need for frequent changing of the dressing, preclude the use of strenuous means to secure the bandage, such as excessive taping and pressing to mold gauze material to the newly circumcised penis. The application of ordinary bandaging materials to the penis of an infant can therefore be awkward, and such a bandage can easily fall off, leaving the infant susceptible to infection.

In the prior art, Scherz, U.S. Pat. No. 5,183,460, relates to a bandage designed to maintain a post-operative penile dressing in place. The bandage disclosed by Scherz is used in conjunction with protective gauze or other surgical dressing. The bandage is substantially L-shaped, the shorter leg portion being divided into three strips. In use, the three segments of the shorter leg portion are adhered to the skin adjacent to the base of the penis, and the longer leg portion is wrapped circumferentially around the penis so as to hold the gauze in place.

Several examples of tubular or sleeve-like bandages exist in the prior art. Scholl, U.S. Pat. No. 2,646,796, discloses a tubular bandage in which the interior surface is coated with a self-bonding adhesive material. The bandage is secured in place by pressing the outer edges of the bandage together so as to seal them, thereby obviating the need for a fastening device. Delao, U.S. Pat. No. 5,592,953, discloses a tubular sleeve secured by drawstrings on either end, the primarily function of which is to protect the bandaged area from water contamination while bathing.

Sleeve-like devices which are secured by Velcro® straps are disclosed in Lemon, U.S. Pat. No. 3,710,790, and Smith, III, U.S. Pat. No. 5,085,210. Both devices are intended for use as a brace for muscle or joint injuries.

None of the patents cited above relates to a penile dressing which is suitable for use on the penis of an infant or adult. There remains a need for a post-operative penile dressing configured for placement on the circumcised penis of an infant or adult which can be readily applied and removed without requiring adhesive to contact the skin, and which can also be secured without the use of excessively forceful means.

It is a common practice today to treat circumcision of an infant as a minor operation with very little post-operative care. After the operation, a small amount of petroleum jelly is applied, a piece of gauze is placed on the wound without being secured, and the infant is diapered. The diaper and gauze must be changed approximately every three hours.

Surprisingly, topical antibiotics and anesthetics are not used to dress the wound. Historically, it was believed that the circumcised infant did not experience a great deal of pain. Recent research and the increasing number of adult circumcisions, however, indicate that there is significant pain associated with circumcisions. It would therefore be desirable to apply topical anesthetics to the wound site. To prevent infection, it would also be desirable to apply topical antibiotics to the wound site. In order to avoid excessive handling of the operated area, it would be highly advantageous to provide a post-operative penile dressing which includes topical antibiotics and anesthetics within the dressing.

SUMMARY OF THE INVENTION

It is an object of the invention to provide a surgical dressing for a circumcised penis which is configured to be placed over the penis as a sheath-like cover.

It is another object of the invention to provide a surgical dressing for a circumcised penis that includes an attachment means which maintains the dressing firmly in place without excessive force.

It is yet another object of the invention to provide a surgical dressing for a circumcised penis that includes an attachment means which allows the dressing to be readily and painlessly applied and removed.

It is still another object of the invention to provide a surgical dressing for a circumcised penis which preserves hygienic conditions by providing a means to attach and remove the dressing with a minimal amount of direct skin contact with the wound site and the dressing itself.

It is still another object of the invention to provide a surgical dressing for a circumcised penis which includes topical antibiotics and topical anesthetics within the dressing.

In accordance with the above objects, in one aspect, the invention features a post-operative surgical dressing for bandaging a penis. The dressing includes a flexible sleeve portion having an inner wall defining a lumen sized and shaped to contain the penis, and an outer wall forming the outside surface of the sleeve portion. The sleeve portion can be deformable into a tube-like shape having a first aperture through which the penis can be inserted into the lumen and a second aperture. A urine drainage component, which can be composed of a material through which urine can flow, can be affixed to the sleeve portion over the second aperture. A means for securing the dressing on the penis is also included.

In preferred variations, the dressing further includes a lining attached to the inner wall of the sleeve portion. The lining can be made of a material that prevents adherence of the penis to the dressing (e.g., petrolatum or petrolatum impregnated gauze such as Xeroform), and can also include a topical antiseptic agent and/or a topical anesthetic agent such as lidocaine.

The means for securing the dressing on the penis can include two securement straps, each of which is composed of an elongated strip of material having a free distal end and a proximal end affixed to the sleeve portion. In some variations of this embodiment, the securement straps are elastic. In other variations, a fastener part (e.g., a hook component of a hook and loop type fastener or an adhesive strip covered by a removable protective layer) is attached to the distal end of each securement strap.

The dressing of the invention can have the sleeve portion slit along its length. The closure flap can have a first portion movably affixed to the sleeve portion and a second portion having thereon an adhesive strip. The second portion of the closure flap can be adapted to be affixed to the outside surface of the sleeve portion, thereby securing the dressing on the penis.

The urine drainage component is composed of a material through which urine can flow. For example, this material can be a porous material such as polypropylene mesh, although the invention is not limited in that regard. The material preferably has an aperture with a surface area of about 0.5–3.5 cm$^2$, although the size of the aperture can vary depending upon the overall size of the dressing (e.g., 1 cm$^2$ aperture for infant-sized dressings and 2 cm$^2$ for adult-sized dressings).

In another aspect, the invention features a circumcision wound dressing kit. This kit includes a sterilized dressing (such as the one described above) hermetically sealed within a sterilized envelope. The envelope can be, e.g., a sterilized foil packet or a sterilized paper packet.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION OF THE PREFERRED EMBODIMENTS

Figure 1:
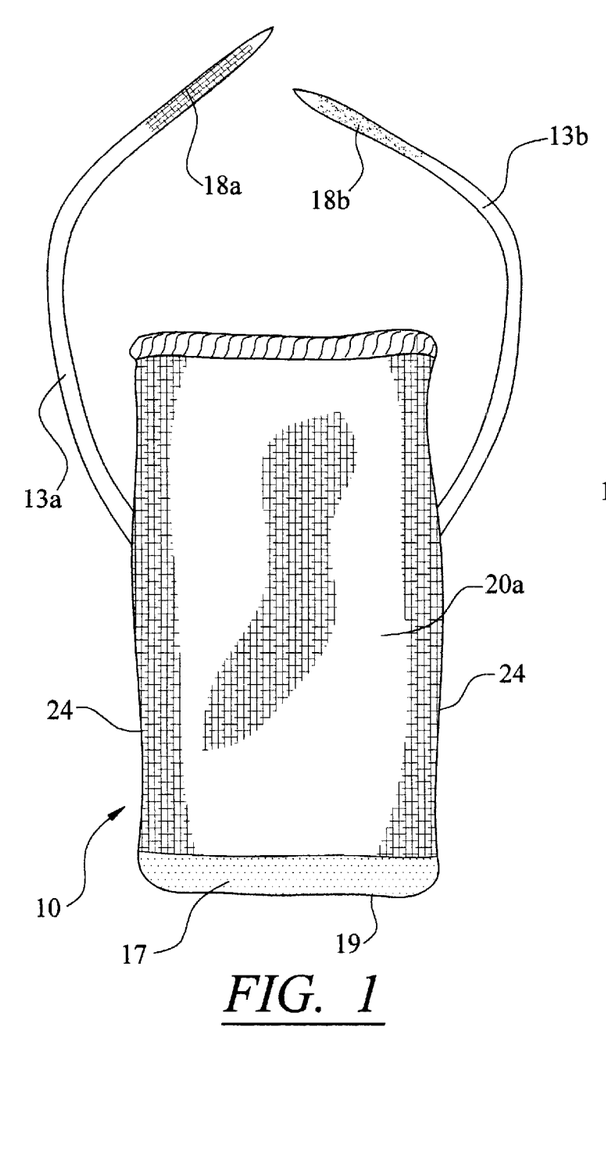
FIG. 1 is a front plan view of the penile dressing prior to use.

A penile dressing in accordance with the inventive arrangements is shown in FIG. 1. The penile dressing comprises a sleeve bandage 10, open at one end. The sleeve bandage 10 is generally flat in shape, and can have outwardly extending securement straps 13a and 13b and a urine drainage component 17 constructed of a highly porous fabric, such as an open weave mesh material. Fastener parts 18a and 18b can be attached to the distal ends of securement straps 13a and 13b respectively, and are comprised of hooked fastening material, for example the hook portion of a Velcro® hoop and loop type fastener. The sleeve bandage 10 can be constructed of any suitable surgical dressing material, such as an open weave gauze, and is sized to fit a penis. For example, the sleeve bandage can be about 2–3 cm in length and about 1–1.5 cm in diameter for an infant, about 3–5 cm in length and about 1.5–3 cm in diameter for an older child, and about 5–10 cm in length and about 3–5 cm in diameter for an adult.

Figure 1A:
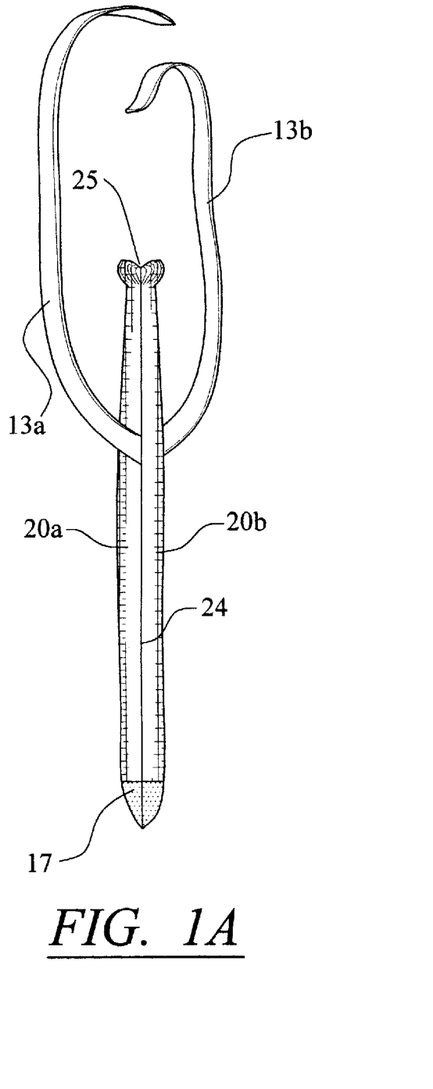
FIG. 1A is a side view of the penile dressing as shown in FIG. 1.
Figure 2:
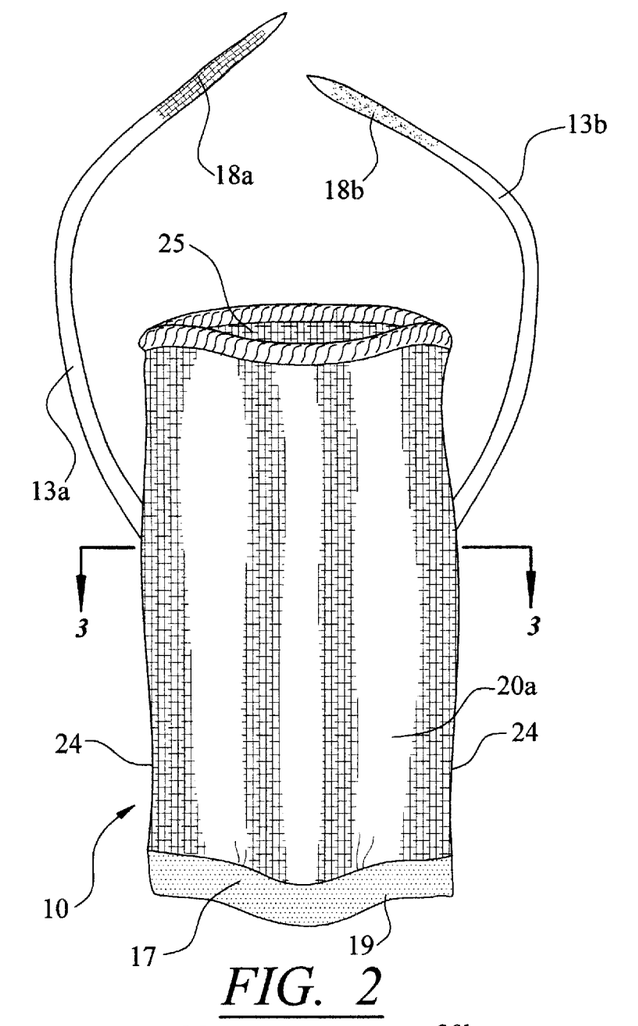
FIG. 2 is a front perspective view of the penile dressing in which the seal has been opened in preparation for use.

As shown in FIG. 1A, the sleeve bandage 10 can be assembled from two opposing gauze material portions 20a and 20b which can be stitched or otherwise adhesively bonded to the urine drainage component 17, and similarly joined at a seam 24 along the sides of the sleeve bandage 10. At the side of the sleeve bandage 10 opposite the urine drainage component 17, there can be an opening 25 formed by gauze material portions 20a and 20b. FIG. 2 illustrates a preferred embodiment of the penile dressing in which the bandage sleeve 10 can be deformed (e.g., by pressing inward at seam 24) into a tube-like shape immediately prior to use. Deforming the sleeve bandage 10 as such enlarges the sleeve opening 25 such that a penis can be inserted through it, into the lumen defined by the inner faces of portions 20a and 20b.

Figure 3:
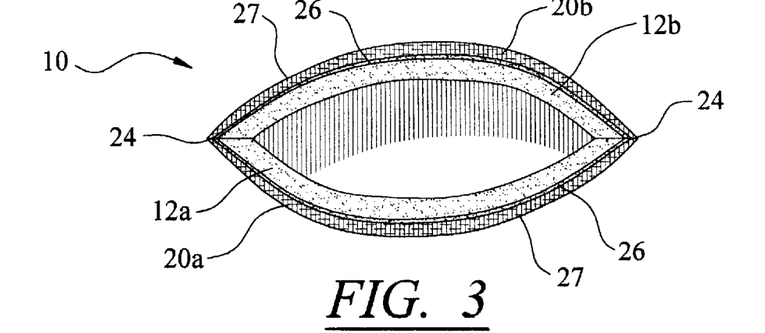
FIG. 3 is a cross-section of the open penile dressing as shown in FIG. 2 taken along line 3–3'.

A preferred embodiment of the interior construction of the sleeve bandage 10 is shown in FIG. 3. In this arrangement, the sleeve bandage 10 includes an outer wall 27 formed by the outside surfaces of the gauze material portions 20a and 20b, and an inner wall 26 formed by the inside portions of opposing gauze material portions 20a and 20b. Lining portions 12a and 12b can be fitted flushly against the inner wall 26 and sandwiched between opposing gauze material portions 20a and 20b. The lining portions may also be stitched or otherwise adhesively bonded to the urine drainage component 17. In a preferred embodiment, lining portions 12a and 12b are comprised of a substance that prevents sticking to skin, e.g., a layer of petrolatum or a sterile non-adhering fine-mesh gauze material impregnated with petrolatum (e.g., petrolatum impregnated gauze with 3% bismuth tribromophenate (Xeroform)). In variations of this preferred embodiment, lining portions 12a and 12b are also impregnated with a topical anti-infective agent such as bacitracin, polymyxin, neomycin, or mixtures of the foregoing such as Neosporin or Polysporin brand anti-infective agents. If short term pain relief is desired, lining portions 12a and 12b can also be impregnated with a topical anesthetic such as 2.5–5% lidocaine (e.g., Xylocaine jelly or ointment), for which the dose is preferably no more than about 9 mg/kg for 2.5% lidocaine and 4.5 mg/kg for 5% lidocaine (generally adults can tolerate a higher dose than infants). In preferred versions of the foregoing the anesthetic is impregnated on only part of lining portions 12a and 12b, e.g, at areas to be in direct contact with the wound. Other materials which provide comfort to the wearer, such as surgical cotton, can also be included.

To prevent the force of a urine stream from dislodging the bandage, the urine drainage component 17 provides an outlet for the urine flow from the penis. In the preferred embodiment, the urine drainage component 17 is made of a porous material, such as polypropylene or a non-absorbent open weave mesh, which allows urine to be channeled out of the bandage and into a diaper or other absorbent pad. In this way, the urine flow is unobstructed, and the absorption of urine into the sleeve bandage 10 can be kept at a minimum.

The securement straps 13a and 13b can be attached to the sleeve bandage 10 in any suitable manner, such as by stitching or adhesively bonding the securement straps 13a and 13b into the side seams 24 of the sleeve bandage 10. The securement straps 13a and 13b can be constructed of any suitable surgical bandage material. In the illustrated embodiment, securement straps 13a and 13b are attached respectively to either side of the sleeve bandage 10, at a position approximately one quarter of the length of sleeve bandage 10 from sleeve opening 25. It is understood, however, that the invention is not limited in this regard. As shown in FIGS. 1 and 2, fastener parts 18a and 18b can be sewn or otherwise adhered to the forward facing surface of the distal ends of the securement straps 13a and 13b, respectively.

In a particularly preferred embodiment, fastener parts 18a and 18b are comprised of hook-type fastening fabric. In this arrangement, the gauze material which comprises the outer surface of the sleeve bandage 10 can approximate the function of loop-type fastening material, and can provide a suitable engagement means for the attachment of fastener parts 18a and 18b to the outer surface of the sleeve bandage 10. Alternatively, a loop type fastener material can be affixed to suitable portions of the sleeve bandage 10 (e.g., along portions 20a and 20b) such that it can securely engage fastener parts 18a and 18b when the sleeve bandage 10 is fitted on a penis.

Figure 4:
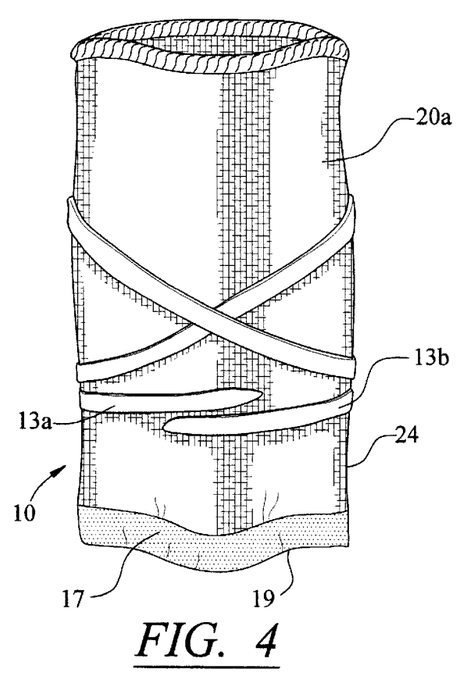
FIG. 4 is a front view illustrating the penile dressing in use with the securement straps wrapped around the penis to hold the dressing in place.
Figure 5:
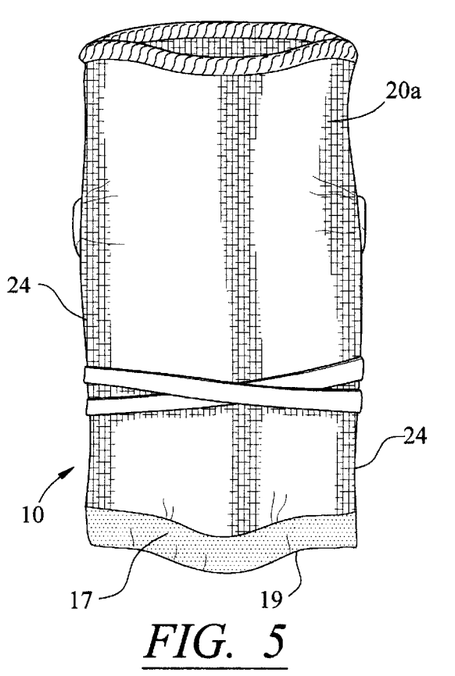
FIG. 5 is a rear view of the penile dressing as shown in FIG. 4.

FIGS. 4 and 5 show the penile dressing in use. To apply the dressing to the circumcised or wounded penis, the sleeve bandage 10 can be slipped over the penis via the sleeve opening 25. The sleeve bandage 10 can be fitted over the length of the circumcised penis so that it is entirely sheathed. To secure the dressing to the penis, the securement straps 13a and 13b can be extended outward so that the fastener parts 18a and 18b face forward. The securement strap 13a can be pulled forward and then wrapped in a generally diagonal direction towards the opposite side of the sleeve bandage 10, and can then be wrapped circumferentially around the penis until the distal end of the securement strap 13a is in contact with the surface of the sleeve bandage 10. The distal end of the securement strap 13a can then be attached to the surface of the sleeve bandage 10 by engaging the fastener part 18a to the gauze material, which can comprise the outer surface of the sleeve bandage 10. The securement strap 13b can then be similarly attached by winding the strap in the opposite direction of the securement strap 13a, and can then be secured by fastener part 18b.

The securement straps 13a and 13b are preferably positioned on and attached to the outer surface of the sleeve bandage 10 so that the penile dressing is retained in place without undue constriction. The relative tackiness of the petrolatum lining, which causes the lining to lightly adhere to the skin, can also help to maintain the dressing in place, so that excessive tightening of the securement straps 13a and 13b is not required.

In a variation of the preferred embodiment of the invention, the securement straps 13a and 13b can be constructed from an elasticized material so as to provide an attachment means with greater firmness. In this variation, the securement straps 13a and 13b can be stretched somewhat before engaging the fastener parts 18a and 18b to the outer surface of the sleeve bandage 10. The securement straps 13a and 13b are preferably somewhat loosely engaged so as not to preclude blood flow.

To remove the dressing, the fastener parts 18a and 18b can be released by gently peeling the hooked fastener material away from the surface of the sleeve bandage 10 until the securement straps 13a and 13b are no longer attached. The securement straps 13a and 13b are then unwound from the sleeve bandage 10, and the dressing can be removed from the penis by grasping the securement straps and pulling the sleeve bandage 10 off the penis.

Figure 6:
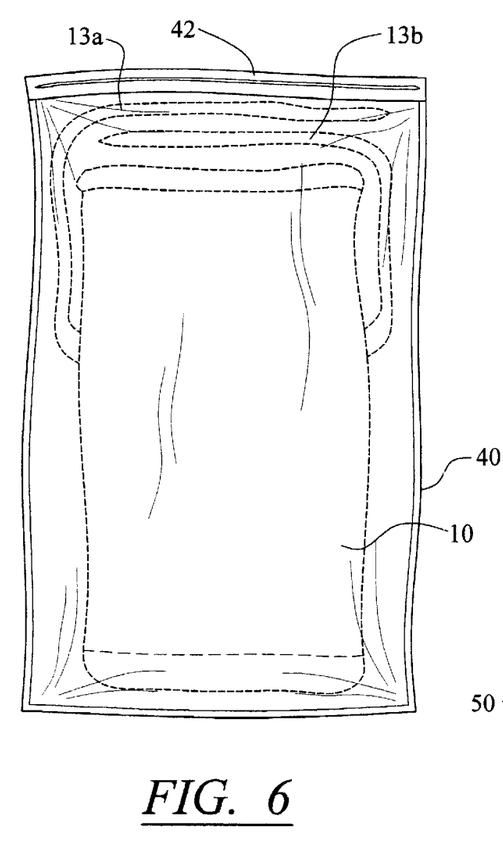
FIG. 6 is an illustration of commercial packaging for the penile dressing, with the dressing shown therein in phantom.

Referring now to FIG. 6, the penile dressing can be packaged so that upon opening the package the dressing can be removed and manipulated by grasping the securement straps 13a and 13b. In this way, direct skin contact with the sleeve bandage 10 can be minimized, which is an aid in preventing possible contamination of the wound site. In FIG. 6, a penile dressing packaged in a foil packet 40 is illustrated. In this preferred embodiment, the dressing and the foil packet 40 are sterilized and the dressing is sealed within the packet 40. The packet 40 can be openable at the top edge 42, preferably by peeling apart the top edges of the packet 40. The dressing can be upwardly oriented within the packet 40 so that prior to opening, the securement straps 13a and 13b can be positioned proximate to top edge 42. Consequently, upon opening the top edge 40, the securement straps 13a and 13b can be grasped, and the dressing can be removed from the packet 40 and applied to the penis with a minimal amount of handling. The packet 40 can be hermetically sealed to prevent entrance of contaminants as well as to prevent desiccation of components of the sleeve bandage 10 prior to use. In a variation of this embodiment, the packaging can be an envelope, such as a sterilized paper envelope.

Figure 7:
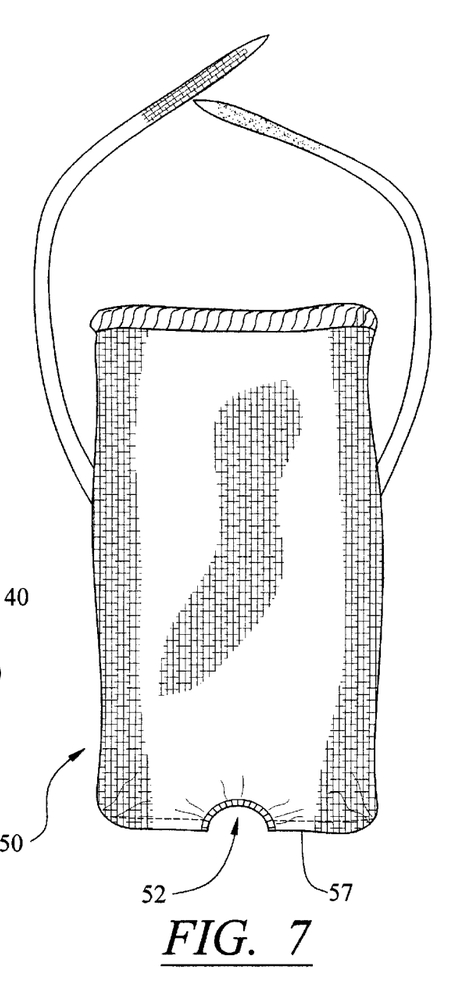
FIG. 7 is an illustration of an alternative embodiment of the penile dressing having an aperture for draining urine.

An alternative embodiment of the penile dressing is illustrated in FIG. 7. In this embodiment, the sleeve bandage 50 can include a circular aperture 52 in the terminal end 57 of the bandage. When positioning the sleeve bandage 50, the aperture 52 is positioned on the penis proximal to the urethra so as to allow the urine to flow through the aperture 52 into a diaper or absorbent pad. The aperture 52 can be of any size suitable for draining urine, such as between about 0.5 and 1.5 $cm^2$.

Figure 8A:
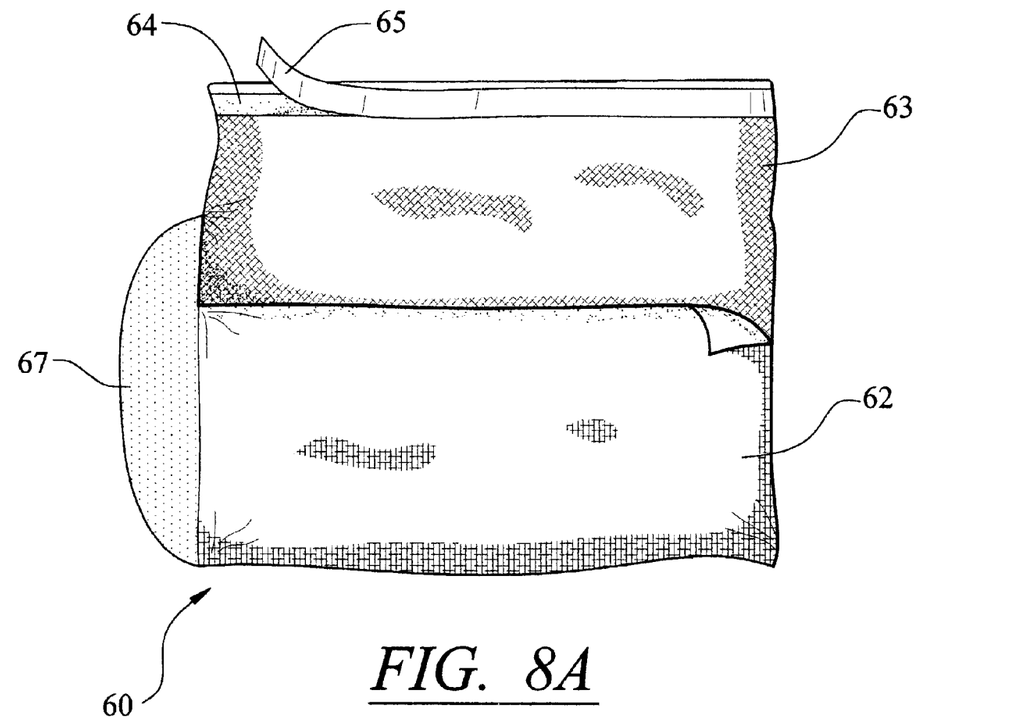
FIGS. 8A and 8B are illustrations of an alternative embodiment of the penile dressing having a single adhesive closure strip.
Figure 8B:
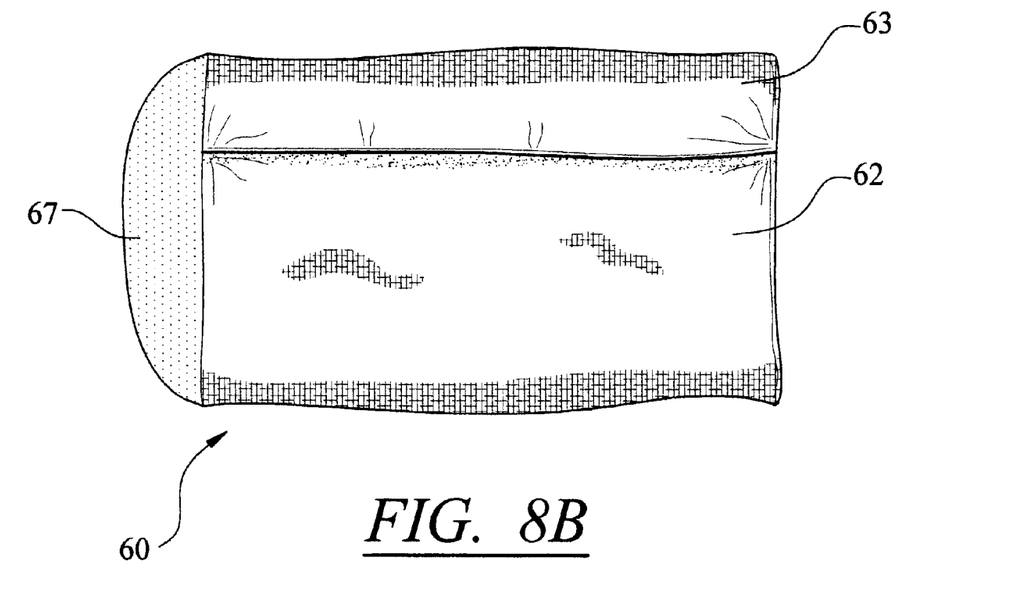

Another alternative embodiment of the invention is shown in FIGS. 8A and 8B. In this embodiment, a penile dressing includes a sleeve bandage 60 made of a gauze material 62 attached to which is a closure flap 63 that includes an adhesive strip 64 covered by a protective layer 65. The gauze material 62 can be fashioned as a single rectangular sheet of surgical dressing material such as cotton gauze. One side of gauze material 62 can be attached to a urine drainage component 67 that can serve as a urine outlet much like the urine drainage component 17 of the preferred embodiment of FIG. 1. The closure flap 63 can be attached to a side of the material 62 adjacent to the portion 67. The other sides of gauze material 62 need not be attached to other components of the sleeve bandage 60 and thus can form a slit along the length of the material 62.

The bandage 60 can be used by slipping the gauze material 62 over a penis such that the material 62 surrounds the penis with the urine drainage component 67 proximal to the glans of the penis and the end opposite portion 67 proximal to the base of the penis. The slit in the material 62 allows bandage 60 to be opened widely at one end to facilitate placement with little trauma to the penis. Protective layer 65 (e.g. a non-sticky strip of plastic that is removably affixed to adhesive strip 64) can be removed from the adhesive strip 64 (e.g. a strip of plastic having an adhesive impregnated thereon), and the flap 63 can then be folded down and secured via the adhesive onto the opposite end of the gauze material 62 to sheath the penis, as shown in FIG. 8B. The adhesive strip 64 can hold the two ends of the gauze material 62 tightly together to secure the sleeve bandage 60 over the penis. The sleeve bandage 60 can be removed by peeling the flap 63 away from the opposite end of the gauze material 62 to loosen the sleeve bandage 60 sufficiently so that it can be easily removed from the penis.

Figure 9A:
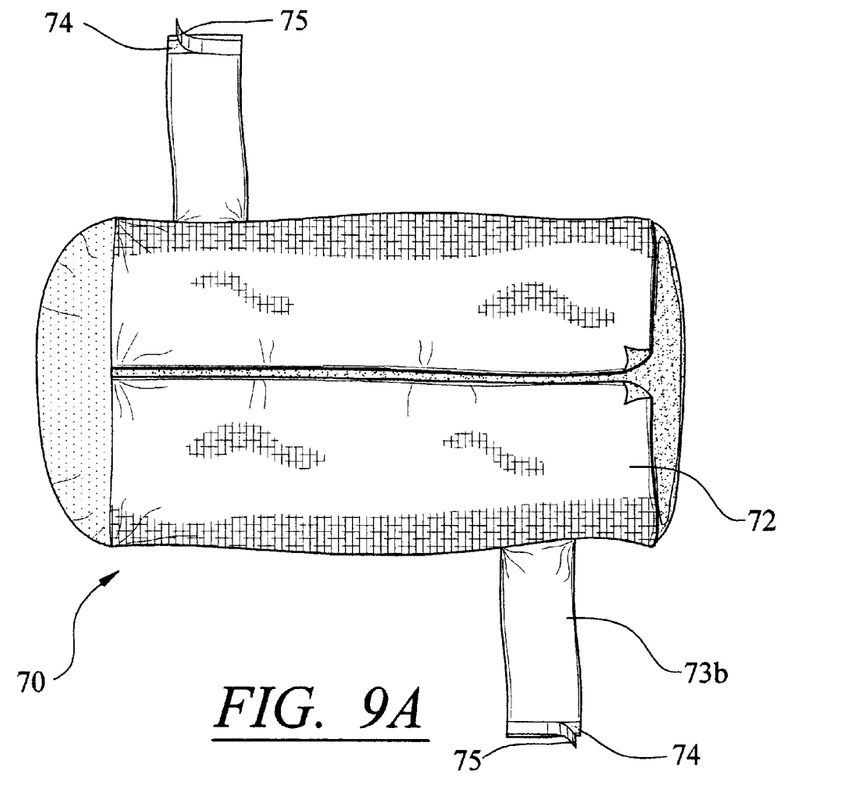
FIGS. 9A and 9B are illustrations of an alternative embodiment of the penile dressing having two adhesive closure straps.
Figure 9B:
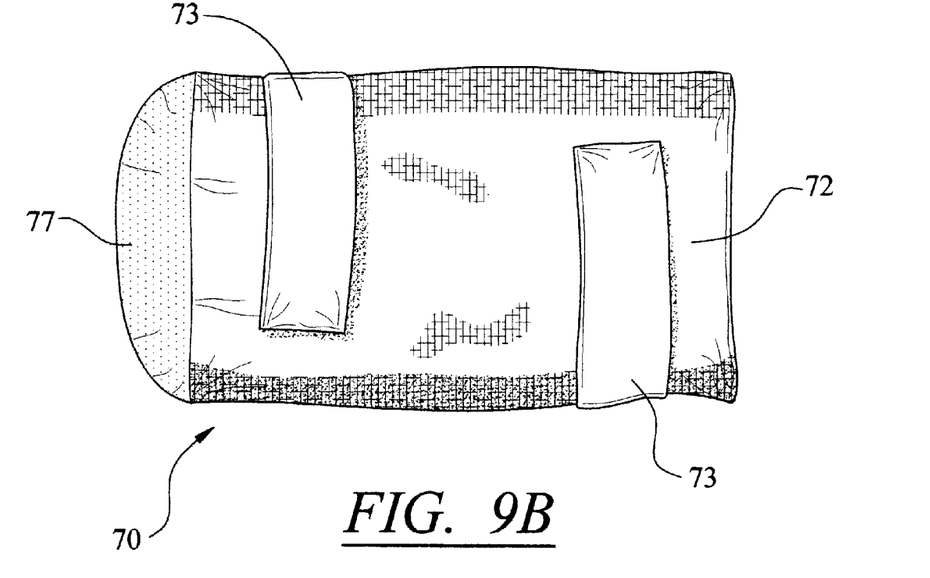

Referring now to FIGS. 9A and 9B, another embodiment of the invention is fashioned similarly to the embodiment described in FIGS. 8A and 8B, except that adhesive securement straps are used in place of the closure flap 63. In this embodiment, a penile dressing includes a sleeve bandage 70 made up of a gauze material 72 attached to which are securement straps 73a and 73b. Each of the securement straps 73a and 73b has an adhesive strip 74 covered by a protective layer 75 at its distal end. Gauze material 72 can be fashioned as a single rectangular sheet of surgical dressing material such as cotton gauze. One side of gauze material 72 can be attached to a urine drainage component 77 that serves as a urine outlet, much like urine drainage component 17 of the preferred embodiment discussed above.

The bandage 70 can be used by the slipping gauze material 72 over a penis such that the material 72 surrounds the penis with the urine drainage component 77 proximal to the glans of the penis and the end opposite portion 77 proximal to the base of the penis. The protective layers 75 (e.g., non-sticky strips of plastic that are removably affixed to adhesive strips 74) can be removed from the adhesive strips 74 (e.g., strips of plastic having an adhesive impregnated thereon), and securement straps 73a and 73b can be wound about the outside of the gauze material 62 to sheath the penis, as shown in FIG. 9B. The adhesive strips 74 can adhere to the material 72 and hold the two ends of the gauze material 72 tightly together to secure the sleeve bandage 70 over the penis. The sleeve bandage 70 can be removed by peeling the securement straps 73 away from their attachment site on gauze material 72 to loosen the sleeve bandage 70 sufficiently so that it can be easily removed from the penis.

This description has been by way of example of how the invention can be made and carried out. Those of ordinary skill in the art will recognize that various details may be modified in arriving at the other detailed embodiments, and that many of these embodiments will come within the scope of the invention. For example, it will be appreciated that the sleeve bandage of the invention is not limited to use as a penile dressing for an infant. It can also be used to treat other penile wounds such as surgical operations involving the penis or traumatic injuries (e.g., lacerations, burns, etc.). It can also be made in a wide variety of sizes to accommodate older children and adults, as well as infants.

Therefore, to apprise the public of the scope of the invention and the embodiments covered by the invention, the following claims are made.

What is claimed is:

1. A dressing for bandaging a penis, the dressing comprising:
    a flexible sleeve portion having an inner wall defining a lumen sized to contain the penis and an outer wall forming the outside surface of the sleeve portion, said sleeve portion being deformable into a tube-like shape defining a proximal tube end having a first aperture though which the penis can be inserted into said lumen and a distal end having a second aperture;
    a urine drainage component affixed to said sleeve portion completely covering said second aperture, said urine drainage component being composed of a porous open-weave mesh material through which urine can flow; and
    securing structure which secures said dressing on the penis, wherein said securing structure comprises at least one securement strap composed of an elongated strip of material having a free distal end and a proximal end, said elongated strip affixed at said proximal end to said sleeve portion between said proximal tube end and said distal tube end, the elongated strip extending in use around at least a portion of the circumference of the penis, the distal end of the elongated strip attachable directly to the sleeve portion to secure the dressing to the penis.

2. The dressing of claim 1, further comprising a lining attached to said inner wall, said lining comprising a material that prevents adherence of the penis to the dressing.

3. The dressing of claim 2, wherein said lining comprises petrolatum.

4. The dressing of claim 2, wherein said lining further comprises a topical anti-infective agent.

5. The dressing of claim 2, wherein said material that prevents adherence of the penis to said dressing comprises a mixture of petrolatum and bismuth tribromophenate.

6. The dressing of claim 2, wherein said lining further comprises a topical anesthetic agent.

7. The dressing of claim 6, wherein said topical anesthetic comprises lidocaine.

8. The dressing of claim 6, wherein said lining further comprises a topical anti-infective agent.

9. The dressing of claim 6, wherein said material that prevents adherence of the penis to said dressing comprises a mixture of petrolatum and bismuth tribromophenate.

10. The dressing of claim 1, wherein said securement straps are elastic.

11. The dressing of claim 1, wherein a fastener part is attached to the distal end of at least one of said securement straps.

12. The dressing of claim 11, wherein said fastener part is the hook component of a hook and loop type fastener.

13. The dressing of claim 11, wherein said fastener part is an adhesive strip.

14. The dressing of claim 13, wherein said adhesive strip has an adhesive portion covered by a removable protective layer.

15. A dressing for bandaging a penis, the dressing comprising:
    a flexible sleeve portion having an inner wall defining a lumen sized to contain the penis and an outer wall forming the outside surface of the sleeve portion, said sleeve portion is slit along its length and is deformable into a tube-like shape defining a proximal tube end having a first aperture through which the penis can be inserted into said lumen and a distal tube end having a second aperture;

a urine drainage component affixed to said sleeve portion completely covering said second aperture, said urine drainage component being composed of a porous open-weave mesh material through which urine can flow; and securing structure which secures said dressing on the penis, wherein said securing structure comprises a closure flap extending along the entire length of the slit, said closure flap having securement means extending along the entire length of said closure flap and attachable to said outside surface of said sleeve portion to secure the dressing to the penis.

16. The dressing of claim 1, wherein said material through which urine can flow comprises an aperture having a surface area of greater than about 0.5 cm².

17. A penile wound dressing kit comprising:

a sterilized dressing hermetically sealed within a sterilized envelope;

said dressing comprising a flexible sleeve portion having an inner wall defining a lumen sized to contain the penis and an outer wall forming the outside surface of said sleeve portion, said sleeve portion being deformable into a tube-like shape having a first aperture through which the penis can be inserted into the lumen and a second aperture;

a urine drainage component affixed to said sleeve portion completely covering the second aperture, said urine drainage component being composed of a porous open-weave mesh material through which urine can flow; and securing structure for securing the dressing on the penis wherein, said securing structure comprises at least one securement strap composed of an elongated strip of material having a free distal end and a proximal end, said elongated strip affixed at said proximal end to said sleeve portion between said proximal tube end and said distal tube end, the elongated strip extending in use around at least a portion of the circumference of the penis, the distal end of the elongated strip directly attachable to the sleeve portion to secure the dressing to the penis.

18. The kit of claim 1, wherein said envelope is a sterilized foil packet.

19. The kit of claim 1, wherein said envelope is a sterilized paper packet.

20. A penile wound dressing kit comprising:

a sterilized dressing hermetically sealed within a sterilized envelope;

said dressing comprising a flexible sleeve portion having an inner wall defining a lumen sized to contain the penis and an outer wall forming the outside surface of said sleeve portion, said sleeve portion is slit along its length and is deformable into a tube-like shape having a first aperture through which the penis can be inserted into the lumen and a second aperture;

a urine drainage component affixed to said sleeve portion completely covering the second aperture, said urine drainage component being composed of a porous open-weave mesh material through which urine can flow; and securing structure for securing the dressing on the penis, wherein said securing structure comprises a closure flap extending along the length of the slit, said closure flap having securement means extending along the entire length of said closure flap and attachable to said outside surface of said sleeve portion to secure the dressing to the penis.

21. The kit of claim 20, wherein said envelope is a sterilized foil packet.

22. The kit of claim 20, wherein said envelope is a sterilized paper packet.

* * * * *